(12) United States Patent
Zhao et al.

(10) Patent No.: US 7,939,681 B2
(45) Date of Patent: *May 10, 2011

(54) METHODS FOR CONVERSION OF CARBOHYDRATES IN IONIC LIQUIDS TO VALUE-ADDED CHEMICALS

(75) Inventors: Haibo Zhao, The Woodlands, TX (US); Johnathan E. Holladay, Kennewick, WA (US); Zongchao C. Zhang, Norwood, NJ (US)

(73) Assignee: Battelle Memorial Institute, Richland, WA (US)

( * ) Notice: Subject to any disclaimer, the term of this patent is extended or adjusted under 35 U.S.C. 154(b) by 828 days.

This patent is subject to a terminal disclaimer.

(21) Appl. No.: 11/774,036

(22) Filed: Jul. 6, 2007

(65) Prior Publication Data

US 2008/0033187 A1      Feb. 7, 2008

Related U.S. Application Data

(60) Provisional application No. 60/836,188, filed on Aug. 7, 2006, provisional application No. 60/851,545, filed on Oct. 13, 2006, provisional application No. 60/938,988, filed on May 18, 2007.

(51) Int. Cl.
*C07D 307/50* (2006.01)
*C07D 307/46* (2006.01)

(52) U.S. Cl. ........................ 549/488; 549/489

(58) Field of Classification Search .................. 549/388, 549/488, 489
See application file for complete search history.

(56) References Cited

U.S. PATENT DOCUMENTS

| | | | |
|---|---|---|---|
| 2,750,394 A * | 6/1956 | Peniston | 549/488 |
| 3,071,599 A * | 1/1963 | Hales et al. | 549/488 |
| 6,518,440 B2 | 2/2003 | Lightner | |

FOREIGN PATENT DOCUMENTS

WO    2006063220 A2    6/2006

OTHER PUBLICATIONS

Dortmund Database Aug. 31, 2005 online: "http://www.ddbst.de/new/downloads/ListOfIonicLiquidsInTheDDB2005-08-31.pdf" accessed May 12, 2010.*
Murugesan et. al. "Ionic Liquids in Carbohydrate Chemistry—Current Trends and Future Directions" Current Organic Synthesis 2005, 2, 437-451.*
Gelas, et. al. "A new method for the preparation of 5-hydroxymethyl-2-furaldehyde by the reaction of ammonium or immonium salts with mono-, oligo- and polysaccharides. Direct access to 5-halomethyl-2-furaldehydes." Carbohydrate Research, 1983, 122(1), 59-68. (translation of pp. 65-66 experimental).*
"Carbohydrate" IUPAC Goldbook 1997, online: "http://www.iupac.org/goldbook/C00820.pdf" accessed May 12, 2010.*
Dieter, et al, Ionic Structure and Interactions in 1-Methyl-3 ethylimidazolium Chloride-A1C13 Molten Salts, J. Am. Chem Soc. 1988, 110, pp. 2722-2726.
Lansalot-Matras, et al., Dehydration of fructose into 5-hydroxymethylfurfural in the presence of ionic liquids, Catalysis Communications, vol. 4, (2003), pp. 517-520.
Moreau, et al., Dehydration of fructose and sucrose into 5-hydroxymethylfurfural in the presence of 1-H-3-methyl imidazolium chloride acting both as solvent and catayst, Journal of Molecular Catalysis A: Chemical 253 (2006) pp. 165-169.
Office Action (Mail Date Jun. 16, 2010) from U.S. Appl. No. 12/110,997, filed Apr. 28, 2008.

* cited by examiner

*Primary Examiner* — Rita J Desai
*Assistant Examiner* — David K O'Dell
(74) *Attorney, Agent, or Firm* — James D. Matheson

(57) ABSTRACT

Methods are described for converting carbohydrates including, e.g., monosaccharides, disaccharides, and polysaccharides in ionic liquids to value-added chemicals including furans, useful as chemical intermediates and/or feedstocks. Fructose is converted to 5-hydroxylmethylfurfural (HMF) in the presence of metal halide and acid catalysts. Glucose is effectively converted to HMF in the presence of chromium chloride catalysts. Yields of up to about 70% are achieved with low levels of impurities such as levulinic acid.

10 Claims, 6 Drawing Sheets

METHODS FOR CONVERSION OF CARBOHYDRATES IN IONIC LIQUIDS TO VALUE-ADDED CHEMICALS

CROSS REFERENCE TO RELATED APPLICATION

This invention claims priority to Provisional application 60/836,188 filed Aug. 7, 2006; Provisional application 60/851,545 filed Oct. 13, 2006; and Provisional application 60/938,988 filed May 18, 2007 incorporated herein their entirety.

This invention was made with Government support under Contract DE-AC05-76RLO1830 awarded by the U.S. Department of Energy. The Government has certain rights in the invention.

FIELD OF THE INVENTION

The present invention relates to methods for conversion of carbohydrates in ionic liquids to value-added chemicals at substantial yields.

BACKGROUND OF THE INVENTION

Replacing petroleum feedstocks with biomass feedstocks will require efficient methods for converting carbohydrates to a diverse number of chemical compounds. A major barrier to achieving this goal is a current inability to effectively utilize 5-carbon (C5) and 6-carbon (C6) carbohydrate building blocks derived from nature as potential feedstocks, including such abundant sugars as, e.g., glucose and fructose. 5-Hydroxymethylfurfural (HMF), an important versatile sugar derivative, is also considered a key intermediate between petroleum-based industrial organic chemistry and bio-based carbohydrate chemistry [Werpy et al. in "Top Value Added Chemicals from Biomass" United States Department of Energy report number DOE/GO-102004-1992; and Kamm et al. "Lignocellulose-based Chemical Products and Product Family Trees" in "Biorefineries-Industrial Processes and Products", 133 pp, Vol. 2 Edited by Kamm, B., Gruber, P. R. & Kamm, M, WILEY-VCH Verlag GmbH & Co. KGaA, Weinheim, 2006]. For example, HMF and its derivatives can potentially replace petroleum-based building blocks [Bicker et al. in Green Chem. 5, 280-284 (2003)] used to make plastics and fine chemicals. However, processes that produce pure HMF from abundant renewable carbohydrates as a basis for biorefinery platforms based on utilization of HMF must produce high yields and have low energy costs. For example, while HMF has been proposed as a key intermediate to produce liquid alkanes from renewable biomass resources [Leshkov et al., Science 312, 1933-1937 (2006)], high production costs currently limit availability and use of HMF industrially. Further, processes that produce HMF involve use of acid catalysts and are essentially limited to fructose as a feed material [Asghari et al., Ind. Eng. Chem. Res. 45, 2163-2173 (2006); Kuster et al, STARCH-STARKE 42, 314-321 (1990); Leshkov et al., Science 312, 1933-1937 (2006); Tyrlik et al., Carbohydr. Res. 315, 268-272 (1999)]. FIG. 1 illustrates a conventional process for acid-catalyzed conversion of carbohydrates. In the figure, conversion of 6-carbon sugars employs concentrated acid (e.g., sulfuric acid) as a catalyst. Acids are corrosive, however, and have drawbacks including product contamination, and difficult recycling and waste disposal issues. Acids further catalyze side reactions leading to byproducts that require complicated product separations for product purification that increase costs. For example, in water under acidic conditions, HMF decomposes to levulinic acid and formic acid, making purification of HMF difficult. Challenges obtaining high yields of dehydration products from conversion of fructose are described, e.g., by Carlini et al. [Applied Catalysis A: General 275 (2004) 111-118].

When glucose is the feed material, HMF yields are usually low [Tyrlik et al., Carbohydr. Res. 315, 268-272 (1999); Watanabe et al., Carbohydr. Res. 340, 1925-1930 (2005)]. Under normal processing conditions, glucose fails to convert to HMF at high yields. Generally, glucose is poorly converted, presumably a consequence of competing reaction pathways that lead to formation of byproducts. With fructose, HMF yield is reported to increase in systems which partition HMF from $H_2O$. For example, HMF yields increase in strong polar organic solvents such as dimethylsulfoxide (DMSO) as part of an aqueous-organic reaction medium [Leshkov et al., Science 312, 1933-1937 (2006)]. In another solvent system, HMF is reported to be formed from fructose in an ionic liquid solvent consisting of [BMIM]$PF_6$ or [BMIM]$PF_4$ with added co-solvent (e.g., DMSO) further including AMBERLYST-15®, an acidic polymer, as catalyst [Lansalot-Matras et al., Catal. Commun. 4, 517-520 (2003)]. In the absence of DMSO co-solvent, best yield of HMF is reported to be 40% to 52%. [Lansalot-Matras et al., Catal. Commun. 4, 517-520 (2003); and Moreau et al., J. Mol. Catal. A: Chem. 253, 165-169 (2006)]. In another system, a specialized ionic liquid, [HMIM]Cl is reported to act as a proton-transfer agent, or acid catalyst [Moreau et al., J. Mol. Catal. A: Chem. 253, 165-169 (2006)].

Polysaccharides (e.g., cellulose) are another class of carbohydrates that are a rich source of carbohydrate building blocks with both high conversion and high yield potential. However, polysaccharides typically require pretreatment to depolymerize the carbohydrates and provide necessary building blocks for conversion. Cellulose, for example, is presently pretreated with acid and subsequently converted to glucose via enzymatic hydrolysis. However, enzyme costs are high and complexity of processing leads to high capital costs. Alternatives such as acid hydrolysis produce by-products which are metabolic poisons to biological fermentation organisms, eliminating fermentation as a route to product conversion. Consequently, while carbohydrates can be converted through various processes including hydrolysis and biological fermentation, poisoning, slow processing, high production costs, and difficult separations result in high processing costs.

Accordingly, there remains a need for new processes that provide conversion of carbohydrates to value-added chemicals and chemical feedstock products at high conversion, high selectivity, and high yields.

SUMMARY OF THE INVENTION

The invention relates to the use of ionic liquids for selective conversion of carbohydrates to value-added chemicals. In one method of the invention, selective conversion of a carbohydrate to value-added chemical(s) includes the steps of: mixing the carbohydrate up to a limit of solubility with an ionic liquid; heating the carbohydrate in the ionic liquid at a reaction temperature in the absence of added catalyst for a reaction time sufficient for conversion of the carbohydrate. Conversion of the carbohydrate produces furans at a substantial yield.

In various embodiments, preferred ionic liquids used as solvents for conversion of carbohydrates have a chemical formula: 1-$R_1$-3-$R_2$-imidazolium chloride ([$R_1R_2$IM]Cl), where $R_1$ and $R_2$ are alkyl groups of formula ($C_xH_{2x+1}$) where X=1 to 18. In another embodiment, ionic liquids include a cation of chemical formula 1-$R_1$-3-$R_2$-imidazolium, where $R_1$ and $R_2$ are alkyl groups of formula ($C_xH_{2x+1}$) where X=1 to 18, and an anion. Anions include, but are not limited to, e.g., halides, sulfates, sulfonates, phosphates, acetates, phosphates, triflates, hexafluorophosphates, tetrafluoroborates, hexafluoroborates, and aluminum chloride. In another embodiment, the anion is methanesulfonate or trifluoromethanesulfonate. In other embodiments, an ionic liquid is 1-ethyl-3-methyl-imidazolium chloride ([EMIM]Cl) or 1-butyl-3-methyl-imidazolium chloride ([BMIM]Cl).

In other embodiments, ionic liquids selected for use include pyridinium salts (e.g., N-alkylpyridinium salts), phosphonium salts (e.g., P,P,P,P-tetraalkylphosphoriium salts), and tetraalkylammonium salts (e.g., N,N,N,N-tetraalkylammonium salts) that include a stoichiometric quantity of a suitable anion, described herein.

In yet other embodiments, carbohydrates including, e.g., monosaccharides (e.g., glucose, fructose, mannose, and galactose, and derivatives thereof, e.g., sorbitol, anhydrosorbitol), disaccharides (e.g., sucrose, maltose, lactose, cellobiose, and derivatives thereof), and polysaccharides (e.g., maltodextrins, starches, cellulose, and derivatives thereof) are converted in the absence of a co-solvent to value-added chemicals including, e.g., furfurals, e.g., 5-hydroxymethylfurfural (HMF).

In still yet other embodiments, 5-carbon sugars (e.g., arabinose, xylose, ribose, and lyxose) are converted to value-added chemicals including, e.g., furfural.

In yet other embodiments, 6-carbon sugars (e.g., glucose, fructose, mannose, and galactose) are converted to value-added chemicals, including, e.g., 5-hydroxymethylfurfurals.

In other embodiments, a furan obtained from conversion of fructose by the process of the invention includes 5-hydroxymethylfurfural (HMF). In another embodiment, a furan is obtained in the absence of a catalyst.

In other embodiments, fructose is converted to HMF in conjunction with a catalyst that is an acid. In other embodiments, fructose is converted to HMF with a catalyst that is a metal halide. Metal halides include, but are not limited to, e.g., $AlCl_3$, $CrCl_2$, $CrCl_3$, $FeCl_2$, $FeCl_3$, CuCl, CuBr, $CuCl_2$, $CuBr_2$, $VCl_3$, $MoCl_3$, $PdCl_2$, $PtCl_2$, $PtCl_4$, $RuCl_3$, $RhCl_3$, and combinations thereof.

Reaction times for conversion of carbohydrates vary, e.g., from about 0.01 minutes to about 300 minutes; or from about 0.01 minutes to about 30 minutes; or from about 0.01 minutes to about 5 minutes. Reaction temperatures for conversion of carbohydrates vary from about 20° C. to about 400° C.; or from about 80° C. to about 250° C.; or from about 100° C. to about 200° C.

In one embodiment, fructose is converted to HMF at a reaction temperature of about 80° C. and a reaction time of between about 1 hour and about 4 hours.

In still yet another embodiment, fructose is converted to HMF at a reaction temperature of about 120° C. and a reaction time of about 180 minutes. In another embodiment, reaction time and reaction temperature is between about 1 hour and about 3 hours at about 120° C.

In yet another embodiment, fructose is converted to HMF in 1-ethyl-3-methylimidazolium [EMIM]$CH_3SO_3$ to which methane sulfonate or its conjugate acid are added as a catalyst. Reaction temperature and reaction time are between about 80° C. for about 2 hours and about 30° C. for about 12 hours.

In another embodiment, conversion of fructose gives a yield of levulinic acid and α-angelicalactone below about 1 percent by weight and more particularly below about 0.1 percent by weight.

In one embodiment, conversion of glucose to HMF proceeds at a reaction temperature of about 100° C. and a reaction time of about 3 hours.

In yet another embodiment, conversion of glucose produces a furan that is furfural.

In another embodiment, the carbohydrate converted is a sugar alcohol yielding a furan that is an anhydrosugar alcohol or a dianhydrosugar alcohol. In another embodiment, the sugar alcohol is sorbitol.

In another embodiment, conversion of carbohydrates is achieved in a batch reactor or a batch reactor system. In other embodiments, conversion of carbohydrates is achieved in a continuous flow reactor or a continuous flow reactor system.

In still yet other embodiments, reaction times and reaction temperatures for conversion of carbohydrates are from about 0.01 minutes at about 400° C. to about 10 h at about 20° C. Conversion of carbohydrates can also be achieved at reaction times of less than or equal to about 0.01 minutes, e.g., in conjunction with a flash conversion process.

In yet other embodiments, conversion of carbohydrates includes a reaction time of from about 0.01 minutes to about 5 hours and a reaction time of from about 400° C. down to about 20° C.

In another embodiment, conversion of glucose to HMF includes a reaction time of from about 0.01 minutes to about 5 hours and a reaction time of from about 400° C. down to about 20° C.

In still yet another embodiment, conversion of carbohydrates is effected in a reaction time of about 0.01 minutes, e.g., in conjunction with a flash conversion process.

In yet another embodiment, carbohydrates are converted in a reaction time and a reaction temperature of between about 0.01 minutes at about 250° C. and about 12 hours at about 20° C.

In various embodiments, conversion of carbohydrates is greater than or equal to about 80 percent and yield of furans is greater than or equal to about 50 percent on a mole basis; or at least about 35 percent by weight.

In another embodiment, conversion of glucose gives yields of levulinic acid and α-angelicalactone of less than about 3 percent by weight.

A more complete appreciation of the invention will be readily obtained by reference to the following description of the accompanying drawings in which like numerals in different figures represent the same structures or elements.

DETAILED DESCRIPTION OF THE INVENTION

Figure 1:
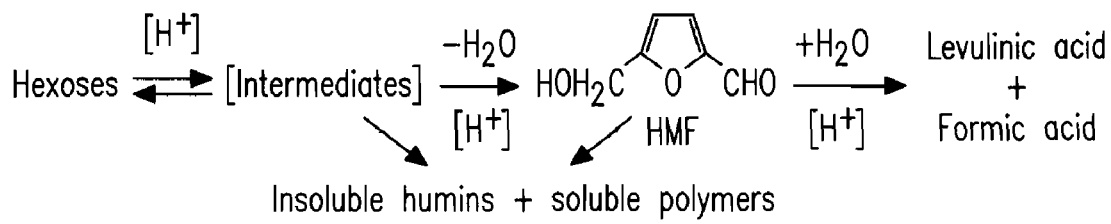
FIG. 1 (Prior Art) illustrates a process for conversion of carbohydrates to HMF by conventional acid catalyzed dehydration.

The term "Imidazoles" as used herein refers to the class of heterocyclic aromatic compounds of general structural formula [A]:

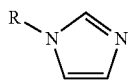
[A]

where R represents functional groups as will be understood by those of skill in the chemical art.

The term "Imidazole" [CAS No. 288-32-4] [Mol. Wt.: 68.08] as used herein refers to the chemical compound of chemical formula ($C_3H_4N_2$) having general structural formula [B]:

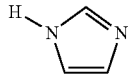
[B]

The term "Imidazolium" as used herein refers to the cationic portion of ion-forming salts from the imidazole class of organic compounds, having general structural formula [C]:

[C]

where $R_1$ and $R_2$ are alkyl groups of formula ($C_xH_{2x+1}$) where X=1 to 18.

The terms "Furans" and "a Furan" as used herein refer to compounds from the class of heterocyclic organic compounds having general structural formula [D1] and [D2]:

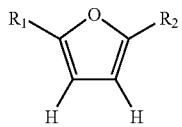
[D1]

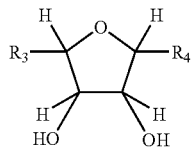
[D2]

where $R_1$, $R_2$, $R_3$, and $R_4$ are functional groups including, e.g., H or C; C may further include O and/or H, defining, e.g., aldehyde or alcohol functional groups. "Furan" [CAS Number 110-00-9] ($C_4H_4O$) is included in this class of compounds having structural formula [D1], where $R_1$ and $R_2$ are H.

The term "Sugar Alcohols" as used herein refers to compounds of chemical formula [$C_nH_{2n+2}O_n$] where n=1, 2, 3, etc. General structural formulas for representative 5-carbon and 6-carbon sugar alcohols are illustrated in [E1] and [E2]:

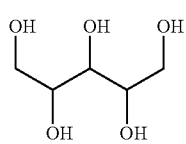
[E1]

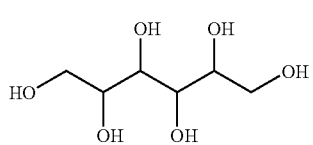
[E2]

The term "Anhydro sugar alcohols" as used herein refers to compounds having general structural formula [F1] and [F2]:

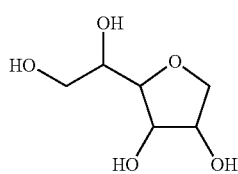
[F1]

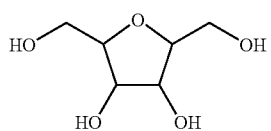
[F2]

The term "Dianhydrosugar alcohols" as used herein refers to compounds having general structural formula [G]:

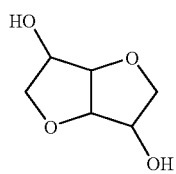
[G]

While preceding compounds have been illustrated using generalized structures, no limitation to specific stereoisomers is implied.

Abbreviation nomenclature used herein to denote ionic liquids identifies the cationic portion of the ionic liquid, e.g., 1-ethyl-3-methyl-imidazolium, by bracket, e.g., [EMIM] or [EMIM]$^+$. The anionic portion of the ionic liquid, e.g., chloride (Cl or Cl$^-$) is identified by placement outside the bracket (e.g., [EMIM]Cl or [EMIM]$^+$Cl$^-$). Unless otherwise noted, nomenclature for ionic liquids with or without ionic charges are used interchangeably, e.g., [EMIM]$^+$Cl$^-$ or [EMIM]Cl.

The term "triflates" has reference to chemical compounds that include a trifluoromethanesulfonate functional group (CF$_3$SO$_3^-$) or a corresponding acid conjugate (CF$_3$SO$_3$H).

The term "Selectivity" as used herein is defined by equation [1]:

$$\text{Selectivity} = \left( \frac{\text{Moles Product Formed}}{\text{Moles Starting Material Reacted}} \right) \quad [1]$$

The term "Conversion" as used herein is defined by equation [2]:

$$\text{Conversion} = 1 - \left( \frac{\text{Moles Unreacted Starting Material}}{\text{Moles Starting Material}} \right) \quad [2]$$

The term "Yield" as used herein is defined by equation [3]:

$$\text{Yield} = \left( \frac{\text{Moles Product Formed}}{\text{Moles Starting Material}} \right) \quad [3]$$

Ionic Liquids

Ionic liquids (IL) suitable for use as solvents in conjunction with the invention provide solubility to the carbohydrates selected for conversion therein. Properties of the ionic liquid solvents vary according to the cationic, alkyl, and anionic group constituents of the liquids. Preferred ionic liquids include salts of the 1-R$_1$-3-R$_2$-imidazolium class of compounds, where R$_1$ and R$_2$ are alkyl groups of formula (C$_x$H$_{2x+1}$) where X=1 to 18, further including a stoichiometric quantity of a selected anion. In these ionic liquids, the cationic portion (or cation) of the ionic liquid includes a 5-member imidazolium ring and alkyl groups R$_1$ and R$_2$. The anionic portion (or anion) of the ionic liquid can vary. Anions include, but are not limited to, e.g., halides including, e.g., chloride (Cl$^-$), bromide (Br$^-$), and iodide (I$^-$); halogen-free anions, including, e.g., sulfates, sulfonates (e.g., alkyl sulfonates), phosphates, acetates, and triflates (e.g., alkyl triflates); hexafluorophosphates (PF$_6^-$); tetrafluoroborates (BF$_4^-$); hexafluoroborates (BF$_6$—); and aluminum chloride (AlCl$_4^-$). Other ionic liquids suitable for use include pyridinium salts (e.g., N-alkylpyridinium salts), phosphonium salts (e.g., P,P,P,P-tetraalkylphosphonium salts), and tetralkylammonium salts (e.g., N,N,N,N-tetraalkylammonium salts) that include a stoichiometric quantity of a suitable anion, described herein.

Ionic liquids can contain impurities that are catalytic. In an illustrative example, reactivity of a carbohydrate in an "as-received" [EMIM]CH$_3$SO$_3$ ionic liquid had high activity due to presence of contaminants and/or impurities in the ionic liquid. However, when the "as-received" ionic liquid was purified to remove contaminants and/or impurities, reactivity of the carbohydrate was negligible. In general, at low reaction temperatures, catalysts are required for conversion of carbohydrates in ionic liquids.

Conversion of fructose to HMF is demonstrated using three exemplary [AMIM]Cl ionic liquid solvent systems, where A is an alkyl group, including, but not limited to, e.g., ethyl, butyl, octyl, and the like. Corresponding ionic liquids are: 1-ethyl-3-methylimidazolium [EMIM]Cl; 1-butyl-3-methylimidazolium chloride [BMIM]Cl; and 1-octyl-3-methylimidazolium chloride [OMIM]Cl, but is not limited thereto. These ionic liquids are preferred ionic liquid (IL) solvent systems for conversion of carbohydrates to versatile chemicals at high yields, including, e.g., 5-hydroxymethylfurfural (HMF).

In one process, according to an embodiment of the invention, fructose is converted in the presence of metal halide catalysts to HMF at high yields. In another process, fructose is converted to HMF at selected reaction temperatures in the absence of any added catalyst. In another process, fructose is converted in the presence of a mineral acid to HMF at high yields.

Conversion of 6-Carbon Sugars

Conversion of 6-C sugars (e.g., glucose and fructose) to HMF in ionic liquids has been demonstrated.

Figure 2:
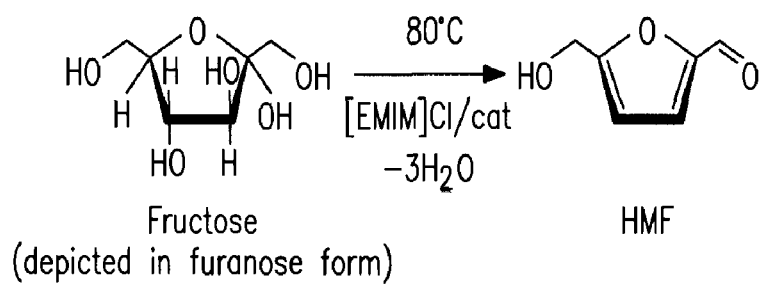
FIG. 2 illustrates a reaction process for conversion of fructose to HMF in an exemplary ionic liquid, with added metal halide catalysts to promote desired chemistry, according to embodiments of the process of the invention.

FIG. 2 illustrates a reaction process for conversion of fructose to HMF in an exemplary ionic liquid, [EMIM]Cl, with metal halide catalysts or acid catalysts added to promote desired chemistry. While the furanose form of fructose is illustrated in the figure, other forms of fructose (e.g., pyranose forms) are equally converted. Thus, no limitations are intended.

In a preferred embodiment, in the ionic liquid [EMIM]Cl, reaction time and reaction temperature is about 1 h to 3 h at about 80° C., but is not limited thereto. For example, reaction times and reaction temperatures may be selected in the range from about 0.01 minutes at 400° C. to about 12 h at 80° C. Alternatively, reaction times and reaction temperatures may be selected in the range from about 0.01 minutes at 250° C. to about 8 h at 80° C.

In other ionic liquids, the melting point is lower, allowing for a lower reaction temperature. For example, [EMIM]CH$_3$SO$_3$ is a liquid at room temperature. Reaction times and reaction temperatures may be selected at between about 20 h at 20° C. and from about 0.01 minutes at 250° C.

Continued processing of product furans may lead to formation polymeric products that are easily separated from products of interest.

Figure 3:
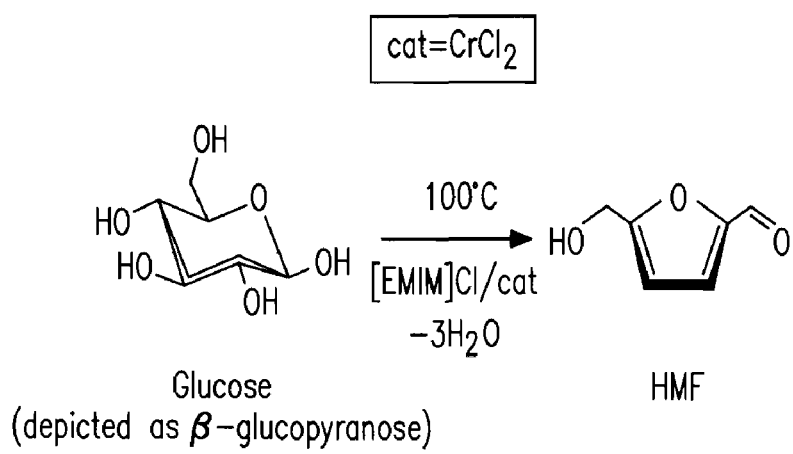
FIG. 3 illustrates a reaction process for conversion of glucose to HMF in an exemplary ionic liquid, with added $CrCl_2$ metal halide catalyst to promote desired chemistry, according to another embodiment of the process of the invention.

FIG. 3 illustrates a reaction process for conversion of glucose to HMF in an exemplary ionic liquid, e.g., ([EMIM]Cl), with CrCl$_2$ metal halide catalyst added, according to another embodiment of the process of the invention. As illustrated in the figure, in the ionic liquid treated with CrCl$_2$ metal halide catalyst, conversion of glucose to HMF occurs.

In a preferred embodiment, a reaction time and a reaction temperature are 3 h at about 100° C. are used, but is not limited thereto. For example, reaction temperatures and reaction times may be selected in the range from 1 minute to about 20 minutes at 150° C. or about 0.01 minutes at 250° C.; or 0.01 minutes at about 400° C.

In other embodiments, hydrolysis of cellulose to glucose, dehydration of glucose to HMF has been demonstrated. In a preferred embodiment, a reaction time and a reaction temperature of In a preferred embodiment, a reaction time and reaction temperature are 0.5 h at about 140° C. is used, but is not limited thereto. For example, reaction temperatures and reaction times may be selected in the range from about 5 minutes and about 200° C.; or about 0.1 minutes at about 250° C.; or about 0.01 minutes at about 400° C.

Figure 4:
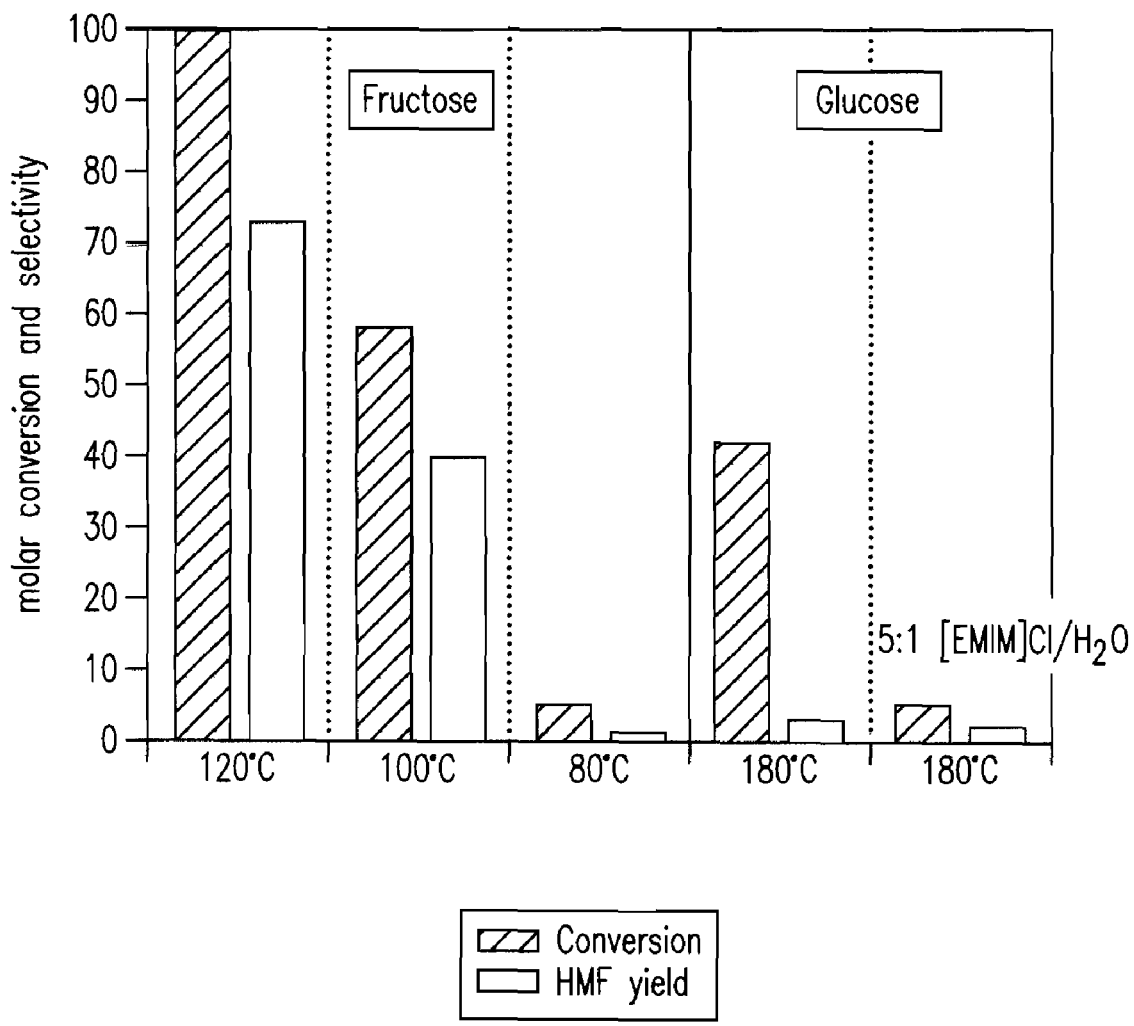
FIG. 4 is a plot comparing conversion results for fructose and glucose to HMF as a function of temperature, according to different embodiments of the process of the invention.

FIG. 4 is a histogram that compares conversion results for fructose and glucose to HMF as a function of temperature in an exemplary ionic liquid, [EMIM]Cl, with no added catalyst. As shown in the figure, at sufficiently high temperatures, fructose is converted to HMF, with yields that decrease in the temperature range between about 120° C. and about 80° C. In contrast, glucose does not produce any significant quantity of HMF, even at 180° C. When water is added to the solvent ([EMIM]Cl) at a ratio of about 5:1, glucose is effectively inert.

A wide range of metal halide catalysts can be added to increase yields of desired end products. Fructose, for example, is rapidly converted to HMF in ionic liquids treated with metal halide catalysts. The catalysts provide efficient conversion. In such reactions, a very low quantity of levulinic acid impurity is formed, typically below about 1% and more particularly below about 0.1%.

In yet other processes, high yields of HMF are obtained from conversion of glucose in ionic liquids with a metal halide catalyst added. Chromium chlorides (e.g., $CrCl_2$ and $CrCl_3$) are uniquely effective catalysts for selective conversion of glucose to HMF, providing yields of greater than or equal to about 70%, described further herein.

In still yet other embodiments, HMF is produced from conversion of complex biomass materials, including e.g., cellulose in ionic liquid solvents Yields of approximately 50% are obtained.

While the exact mechanism for action of metal halide catalysts is unknown in these processes, at catalytic quantities of catalyst (e.g., 0.5% by weight), the ionic liquid solvent is believed to employ an equimolar amount of ionic liquid (e.g., [EMIM]Cl) and the associated metal halide. For purposes of illustration, addition of $CrCl_2$ in the ionic liquid [EMIM]Cl proceeds as denoted in equation [4]:

$$[EMIM]^+Cl^- + CrCl_2 \rightarrow [EMIM]^+CrCl_3^- \quad [4]$$

Experiments Demonstrating Conversion of Fructose to HMF in Ionic Liquids Treated with Metal Halide Catalysts Fructose conversion in ionic liquids treated with and without addition of a catalyst demonstrates broad applicability and advantages of the processes of the invention described herein. For example, fructose can be selectively dehydrated to 5-hydroxymethylfurfural (HMF) with low yields of levulinic acid if treated with metal halide catalysts, described further hereafter.

Catalysts. Metal halide catalysts were tested using a high pressure reactor (e.g., a Symyx® high pressure reactor system equipped with a heated orbital shaker, Symyx Technologies Inc., Santa Clara, Calif., USA), but is not limited thereto. Ionic liquids and selected catalysts and were to reaction vials by mass. Vials were shaken at 700 rpm and heated at 150° C. between about 10 min. and 30 min. (0.5 h) to mix ionic liquid and catalyst.

Protocol. Fructose was added to reaction vials and introduced to the reactor. The reactor was purged at room temperature with $N_2$ or air, heated to an operating temperature of 80° C., and shaken at 700 rpm for 3 h, before cooling and venting.

Sample Analysis. 500 μL of water was added to each reaction vial followed by centrifugation at 3000 rpm for 30 min. Samples were then diluted with water by a factor of two for analysis by high pressure liquid chromatography (HPLC). For initial analyses, samples were injected onto an Aminex Fast Acid column and analyzed by refractive index on an Agilent 1100 series HPLC using a flow rate of 1 mL/min, column temperature of 60° C., and a 0.005M $H_2SO_4$ mobile phase. Select samples were chosen from the primary HPLC screen for a secondary HPLC analysis on a long column (e.g., an Aminex® model HPX-87H, 7.8 mm×300 mm, 9 μm particle size, column available commercially from Bio-Rad Laboratories, Richmond, Calif., USA) at a flow rate of 0.55 mL/min, a temperature of 60° C., and a 0.005M $H_2SO_4$ mobile phase. HPLC results were recorded and used to calculate feed conversion percentages, product selectivity, and molar balances. Catalysts were also ranked for effectiveness. Preferred catalysts, for example, exhibited high conversion and good selectivity yields to HMF.

Figure 5:
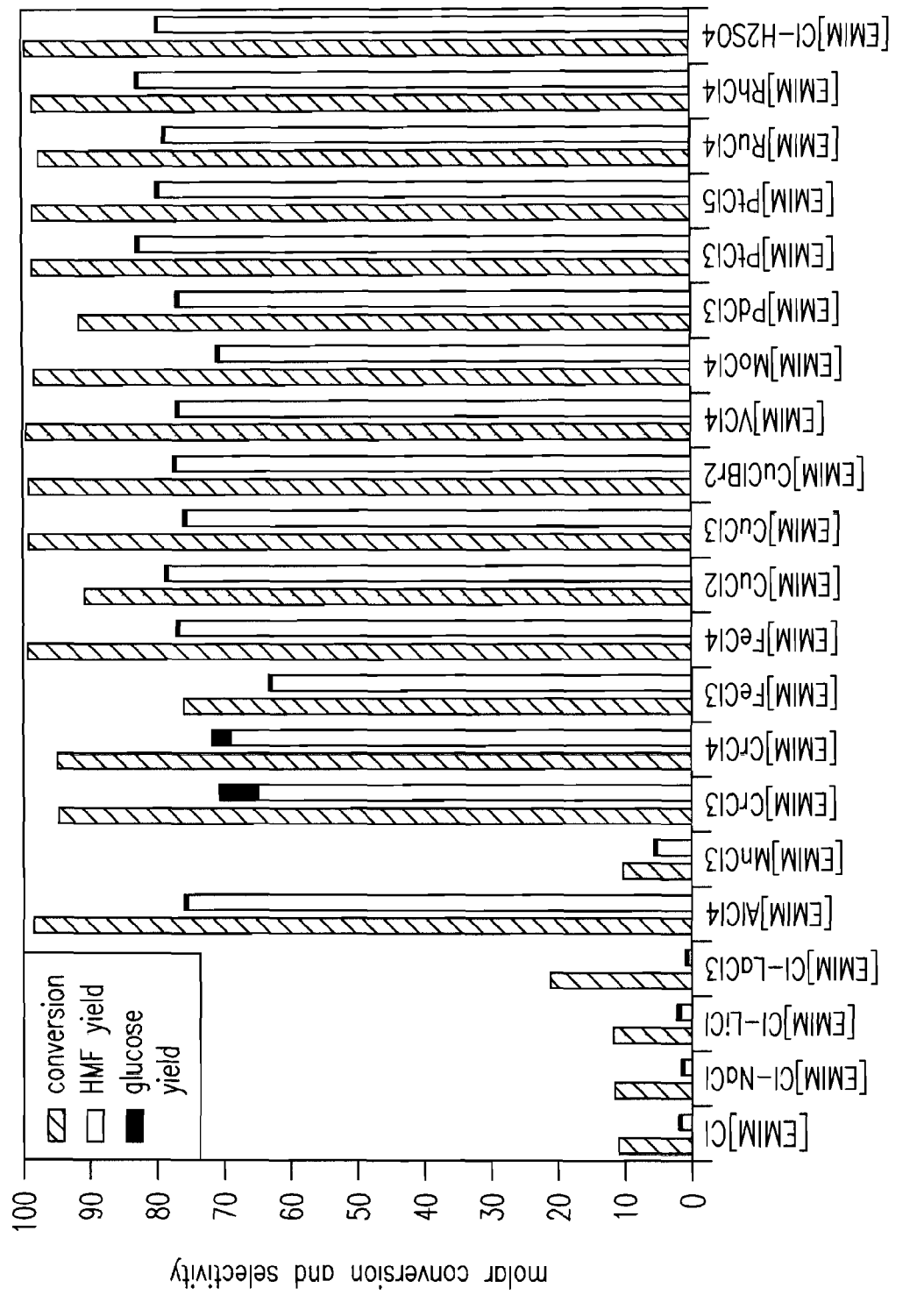
FIG. 5 is a plot showing conversion results for fructose in an exemplary ionic liquid treated with various metal halide catalysts, according to different embodiments of the process of the invention.

FIG. 5 is a histogram showing conversion results for fructose in an exemplary ionic liquid treated with various metal halide catalysts, according to different embodiments of the process of the invention. In the figure, metal halide catalysts included: $CrCl_2$, $CrCl_3$, $FeCl_2$, $FeCl_3$, CuCl, $CuCl_2$, $VCl_3$, $MoCl_3$, $PdCl_2$, $PtCl_2$, $PtCl_4$, $RuCl_3$, or $RhCl_3$. As shown, dehydration of fructose to HMF is catalyzed by many metal halide catalysts and mineral acids, e.g., sulfuric acid, ($H_2SO_4$). Two metal halides were ineffective, i.e., $LaCl_3$, and $MnCl_2$. Alkali metal halides (e.g., NaCl, and LiCl) were also ineffective. HMF yields from conversion of fructose ranged from about 63% to about 83% at reaction times of about 3 h at 80° C. Product mixtures were very clean, as evidenced by NMR analysis. For example, yields of levulinic acid and α-angelicalactone were low, typically less than about 0.1%.

Conversion of Glucose to HMF

Conversion experiments for fructose were repeated using glucose as a feed material. Temperature was raised to 100° C. due to a lower expected reactivity of glucose relative to fructose.

Figure 6:
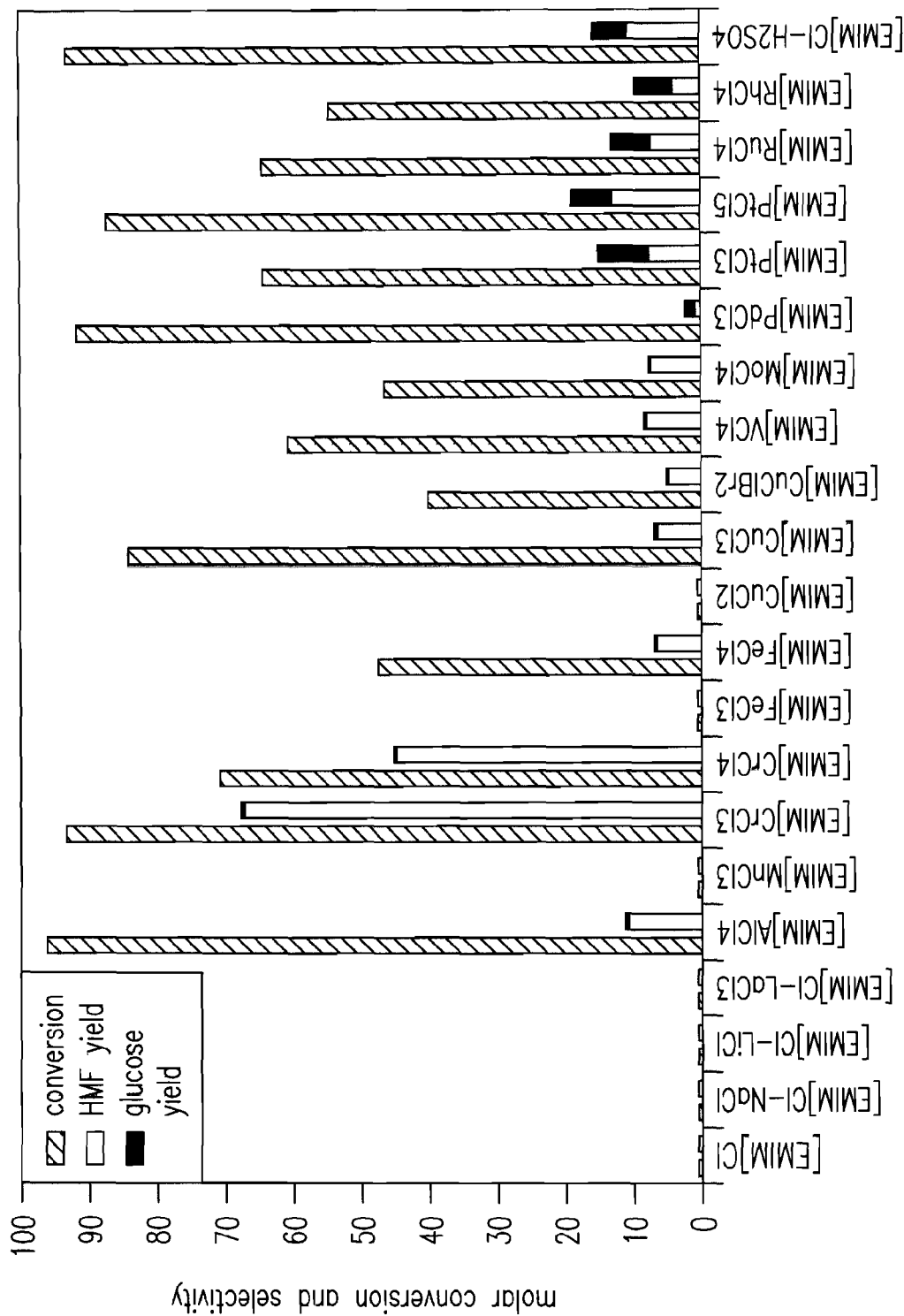
FIG. 6 is a plot showing conversion results for glucose in an exemplary ionic liquid treated with various metal halide catalysts, according to different embodiments of the process of the invention.

FIG. 6 is a histogram showing conversion results for glucose in an exemplary ionic liquid, [EMIM]Cl, pretreated with various metal halide catalysts. As shown in the figure, Glucose conversion was high for many of the metal halide catalysts tested, including $AlCl_3$, $FeCl_3$, $CuCl_2$, CuCl, $VCl_3$, $MoCl_3$, $PtCl_2$, $PtCl_4$, $RuCl_3$, and $RhCl_3$. These metal halides showed a conversion of glucose of 40% or greater. However, HMF yields were low. HMF yields from conversion of glucose were also low using acids (e.g., $H_2SO_4$) as catalysts. One catalyst, $CrCl_2$, gave HMF yields of 68-70%, a previously elusive efficiency for conversion of glucose. HMF yields for ionic liquid solvent systems not containing $CrCl_2$ or $CrCl_3$ were on the order of 10%. HMF yields could not be accounted for by product instability under reaction conditions. Results indicate that high conversion of glucose is achieved with various metal halide catalysts, in many ionic liquid systems. However, low product yields suggest these metal halides catalyze undesired reaction pathways.

Conversion of Glucose in Ionic Liquid Containing Metal Halide Catalysts $CrCl_2$, $CuCl_2$, and $FeCl_2$ In additional experiments, conversion of glucose was tested for three specific catalysts, $CrCl_2$, $CuCl_2$, and $FeCl_2$, at 100° C. To ensure uniform catalyst loading, each catalyst-ionic liquid mixture was prepared in a single batch and then added to the reaction vial (500 mg aliquots) containing glucose (50 mg). Following reaction times at selected reaction temperatures, samples were analyzed by HPLC.

Figure 7:
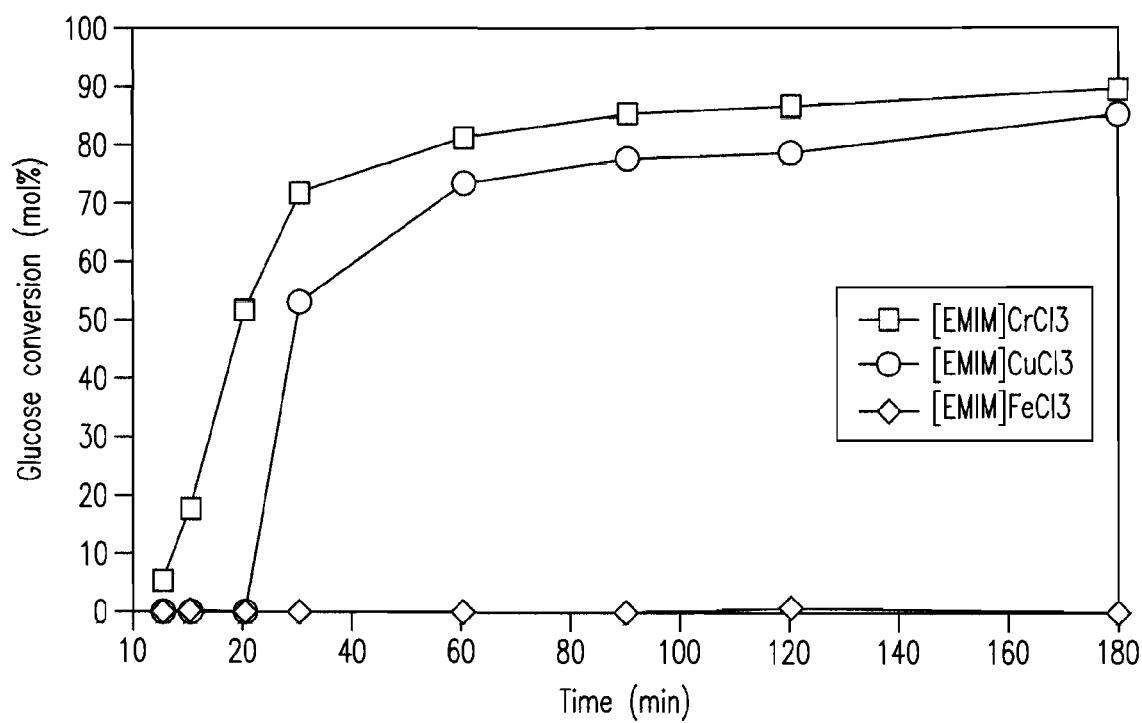
FIG. 7 is a plot showing conversion results for glucose as a function of time in an exemplary ionic liquid treated with $CrCl_2$, $CuCl_2$, and $FeCl_2$ metal halide catalysts.

FIG. 7 plots glucose conversion (mol %) in [EMIM]Cl ionic liquid treated with each of three metal halide catalysts, i.e., $CrCl_2$, $CuCl_2$, and $FeCl_2$, respectively, as a function of time. Glucose conversion is highest in ionic liquid containing $CrCl_2$. Glucose is reactive in ionic liquid containing $CuCl_2$, but does not provide a high yield of HMF. In ionic liquid containing $FeCl_2$, glucose shows essentially no reactivity. Results suggest chemistry for conversion of the carbohydrate differs for each of the metal halide catalysts tested. Effectiveness of $CrCl_2$ catalyst for conversion of glucose to HMF was unexpected.

Figure 8:
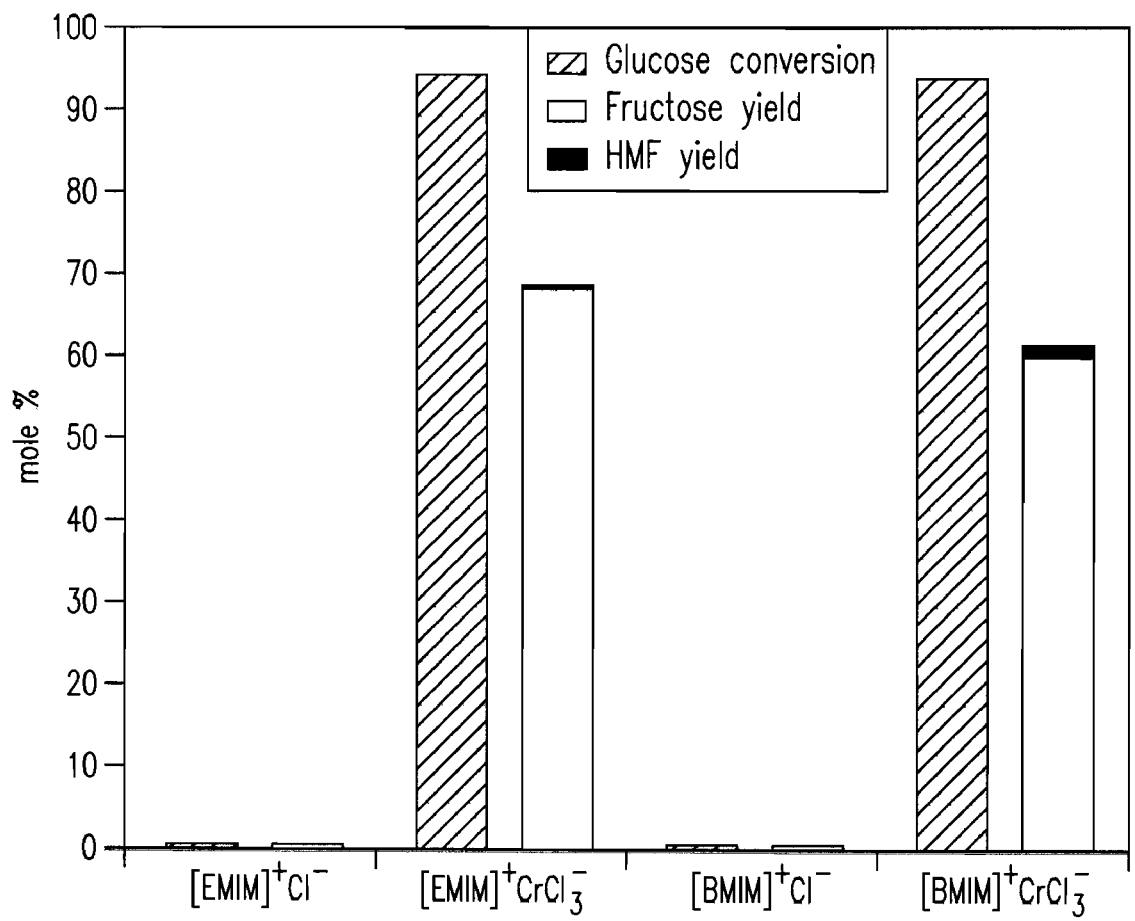
FIG. 8 is a plot presenting conversion results for glucose in an exemplary ionic liquid treated with $CrCl_2$ metal halide catalyst, according to a preferred embodiment of the process of the invention.

FIG. 8 is a histogram showing results for conversion of glucose in two exemplary ionic liquids, [EMIM]Cl and [BMIM]Cl, treated with a preferred metal halide catalyst, $CrCl_2$. As shown in the figure, conversion of glucose is greater than 90% (mole basis), with yields of HMF of about 68% (in [EMIM]Cl) and 60% (in [BMIM]Cl), respectively.

Conversion of Cellulose

Conversion of cellulose in an ionic liquid is described hereafter optionally in conjunction with a catalyst. Ionic liquids catalyze all, or a majority, of the chain of necessary reactions, including, e.g., decrystallization, hydrolysis, and/or dehydration, yielding the desired conversion products. For example, hydrolysis of cellulose in ionic liquids that yields simple sugars including HMF with low yields of levulinic acid was an unexpected result. And, use of additional acids is not required for dehydration to occur. Further, conversion of cellulose and other complex carbohydrates in ionic liquids exhibits high selectivity to desired value-added products. Cellulose can also be converted selectively to other products in different ionic liquids systems. Thus, by appropriate selection of ionic liquid, product can be selectively tuned. Conversion in ionic liquids is applicable to conversion of other carbohydrates and polysaccharides including starch. Thus, the disclosure is not intended to be limited to exemplary embodiments and exemplary carbohydrates described herein.

Following examples provide a further understanding of the invention

EXAMPLE 1

Conversion of Fructose to HMF in [EMIM]Cl

Metal Halide or Acid Catalyst

Fructose (99.9%) was supplied by Mallinckrodt. [EMIM]Cl (99%) was supplied by Solvent-Innovation (GmbH, Cologne, GE). Metal halide catalysts were CuCl, $CuCl_2$, $CuBr_2$, $MOCl_3$, $FeCl_2$, $FeCl_3$, $CrCl_2$, $CrCl_3$, $VCl_3$, $AlCl_3$, $MnCl_3$, $PdCl_2$, $PtCl_2$, $PtCl_4$, $RuCl_3$, $RhCl_3$ were supplied by Sigma-Aldrich (St. Louis, Mo., USA) Acid catalyst was $H_2SO_4$, supplied by Sigma-Aldrich (St. Louis, Mo., USA). 500 mg [EMIM]Cl was loaded into reaction vials. Metal halide catalysts were added to respective vials at a concentration of ~6 mol % with respect to fructose. 2 mg $CrCl_2$ was added to its reaction vial. Vials were installed into the high pressure reactor, heated at 150° C. and shaken at 700 rpm to mix contents. After cooling, 50 mg fructose was added to each vial and heated at 80° C. for 3 h. After cooling, 2.0 mL of water was added for analysis by HPLC. Results are presented in TABLE 1 (see FIG. 5).

TABLE 1

Conversion of Fructose to HMF, and product yields.

| Example | Feedstock | Catalyst | Feedstock conversion (%) | Product yields (%)* |
|---------|-----------|----------|--------------------------|---------------------|
| 1.1 | Fructose | None | 10.92 | HMF: 1.36 |
| 1.2 | Fructose | CuCl | 91.25 | HMF: 78.81 |
| 1.3 | Fructose | $CuCl_2$ | 99.54 | HMF: 76.02 |
| 1.4 | Fructose | $CuBr_2$ | 99.59 | HMF: 77.48 |
| 1.5 | Fructose | $MoCl_3$ | 98.67 | HMF: 70.88 |
| 1.6 | Fructose | $FeCl_2$ | 76.40 | HMF: 63.15 |
| 1.7 | Fructose | $FeCl_3$ | 99.80 | HMF: 77.08 |
| 1.8 | Fructose | $CrCl_2$ | 95.32 | HMF: 65.26 |
| 1.9 | Fructose | $CrCl_3$ | 95.41 | HMF: 69.28 |
| 1.10 | Fructose | $VCl_3$ | 100.00 | HMF: 77.03 |
| 1.11 | Fructose | $AlCl_3$ | 99.00 | HMF: 76.00 |
| 1.12 | Fructose | $MnCl_3$ | 10.22 | HMF: 5.02 |
| 1.13 | Fructose | $PdCl_2$ | 92.00 | HMF: 77.00 |
| 1.14 | Fructose | $PtCl_2$ | 99.00 | HMF: 83.00 |
| 1.15 | Fructose | $PtCl_4$ | 99.00 | HMF: 80.00 |
| 1.16 | Fructose | $RuCl_3$ | 98.00 | HMF: 79.00 |
| 1.17 | Fructose | $RhCl_3$ | 99.00 | HMF: 83.00 |
| 1.18 | Fructose | $H_2SO_4$ | 99.00 | HMF: 80.00 |

*Yields of levulinic acid and α-angelicalactone were less than 0.1% for all experiments.

EXAMPLE 2

Conversion of Fructose to HMF in Alternate Ionic Liquids

Metal Halide or Acid Catalyst

Fructose was processed as in Example 1 in various ionic liquids containing a metal halide or acid catalyst. Ionic liquids were [EMIM]$CH_3SO_3$ (Solvent-Innovations, GmbH, Cologne, GE); tetrabutylammonium chloride (Fluka-Sigma-Aldrich, Steinheim, GE); tetrabutylphosphonium chloride (ionic Liquid Technologies, GmbH, Denzlingen, GE); 1,2,4-trimethylpyrazolium methyl sulfate (Fluka-Sigma-Aldrich, Steinheim, GE). [EMIM]$CH_3SO_3$, tetrabutylphosphonium chloride, and 1,2,4-trimethylpyrazolium methyl sulfate each contained a catalytic quantity of acid. Results are presented in TABLE 2.

TABLE 2

Conversion of Fructose to HMF, and product yields.

| Example | Feedstock | Ionic Liquid (IL) and Catalyst | Feedstock conversion (%) | Product Yields (%) |
|---------|-----------|--------------------------------|--------------------------|---------------------|
| 2.1 | Fructose | IL: [EMIM]$CH_3SO_3$; Catalyst: acid | 99.6 | HMF: 86.5 |
| 2.2 | Fructose | IL: tetrabutylammonium chloride; Catalyst: $VCl_3$ | — | HMF: 59.1 |
| 2.3 | Fructose | IL: tetrabutylphosphonium chloride; Catalyst: acid | — | HMF: 65.2 |
| 2.4 | Fructose | IL: 1,2,4-trimethyl-pyrazolium methyl sulfate; Catalyst: acid | — | HMF: 52.1 |

EXAMPLE 3

Carbohydrate Reactivity in "As-Received" and Purified Ionic Liquid

Carbohydrate reactivity was compared in both "as-received" (as purchased) and purified ionic liquid. Fructose was processed as in Example 1 in 99% [EMIM]$CH_3SO_3$ (Solvent-Innovation, GmbH, Cologne, GE) in both the "as-received" ionic liquid and the ionic liquid purified with basic alumina to remove any contaminants (e.g., methane sulfonic acid). Reaction time and temperature was 3 h at 80° C. Conversion of fructose in the "as-received" ionic liquid was 99.9%; yield of HMF was 83.9%. Conversion of fructose in purified ionic liquid was 0%; yield of HMF was 0%. Results demonstrate that some impurities present in ionic liquids (e.g., as purchased) are sufficient to catalyze reaction of carbohydrates. When purified, the ionic liquid does not exhibit reactivity at the same temperature.

EXAMPLE 4

Conversion of Fructose to HMF in [EMIM]CH$_3$SO$_3$

Acid Catalyst

Fructose was processed as in Example 1 in (99%) [EMIM]CH$_3$SO$_3$ (Solvent-Innovation, GmbH, Cologne, GE) ionic liquid, containing a catalytic quantity of CH$_3$SO$_3$. Liquid products were analyzed by HPLC. Conversion of fructose was 99.6%; yield of HMF was 86.5%; yield of levulinic acid yield was 0.5%. Yields of HMF in repeat experiments ranged from 86% to 90%.

EXAMPLE 5

Conversion of Fructose to HMF in [EMIM]Cl

No Metal Halide or Acid Catalyst

Fructose was processed as in Example 1 in [EMIM]Cl at a reaction temperature of 120° C. for 3 h. Conversion of fructose was 98%; yield of HMF was 73% (see FIG. 4).

EXAMPLE 6

Conversion of Glucose to HMF in [EMIM]Cl

CrCl$_2$ Metal Halide Catalyst

Glucose was processed as in Example 1 at a reaction temperature of 100° C. for 3 h in [EMIM]Cl. Metal halide catalyst was CrCl$_2$. Results are listed in FIG. 6 and TABLE 3.

EXAMPLE 7

Conversion of Glucose to HMF in [EMIM]Cl

CrCl$_3$ Metal Halide Catalyst

Glucose was processed as in Example 1 at a reaction temperature of 100° C. for 3 h in [EMIM]Cl. Metal halide catalyst was CrCl$_3$. Results are listed in FIG. 6 and TABLE 3.

EXAMPLE 8

Conversion of Glucose to HMF in [EMIM]Cl

Various Metal Halide and Acid Catalysts

Glucose was processed as in Example 1 in [EMIM]Cl at a reaction temperature of 100° C. for 3 h. Metal halide catalysts were CuCl, CuCl$_2$, CuBr$_2$, MOCl$_3$, FeCl$_2$, FeCl$_3$, CrCl$_2$, CrCl$_3$, VCl$_3$, AlCl$_3$, MnCl$_3$, PdCl$_2$, PtCl$_2$, PtCl$_4$, RuCl$_3$, RhCl$_3$. Acid catalyst was H$_2$SO$_4$. Results are presented in FIG. 6 and TABLE 3.

TABLE 3

Conversion of Glucose to HMF, and product yields.

| Example | Feedstock | Catalyst | Feedstock conversion (%) | Product yields (%)* |
|---|---|---|---|---|
| 6 | Glucose | CrCl$_2$ | 94.4 | HMF: 68.0 |
| 7 | Glucose | CrCl$_3$ | 71.5 | HMF: 44.3 |
| 8.1 | Glucose | None | 0 | HMF: 0 |
| 8.2 | Glucose | CuCl | 0 | HMF: 0 |
| 8.3 | Glucose | CuCl$_2$ | 85.0 | HMF: 6.4 |
| 8.4 | Glucose | CuBr$_2$ | 40.4 | HMF: 4.7 |
| 8.5 | Glucose | MoCl$_3$ | 46.8 | HMF: 7.2 |
| 8.6 | Glucose | FeCl$_2$ | 0 | HMF: 0 |
| 8.7 | Glucose | FeCl$_3$ | 47.8 | HMF: 6.4 |
| 8.8 | Glucose | VCl$_3$ | 61.2 | HMF: 8.1 |
| 8.9 | Glucose | AlCl$_3$ | 97.3 | HMF: 10.8 |
| 8.10 | Glucose | MnCl$_3$ | 0 | HMF: 0 |
| 8.11 | Glucose | PdCl$_2$ | 20.0 | HMF: 0.7 |
| 8.12 | Glucose | PtCl$_2$ | 65.0 | HMF: 7.6 |
| 8.13 | Glucose | PtCl$_4$ | 88.0 | HMF: 13.0 |
| 8.14 | Glucose | RuCl$_3$ | 65.0 | HMF: 7.1 |
| 8.15 | Glucose | RhCl$_3$ | 55.0 | HMF: 3.9 |
| 8.16 | Glucose | H$_2$SO$_4$ | 94.4 | HMF: 11.0 |

*Yields of levulinic acid and α-angelicalactone were less than 0.1% for all experiments.

EXAMPLE 9

Conversion of Cellulose to HMF in [EMIM]Cl

CrCl$_2$ Metal Halide Catalyst 500 mg [EMIM]Cl, (99.5%) (Solvent-Innovation GmbH, Cologne, Germany) and 0.037 mmol/mL of CrCl$_2$ metal halide catalyst were added to a reaction vial. The vial was heated to 180° C. to create a homogenous catalyst system. 50 mg of cellulose (Sigma-Aldrich, St. Louis, Mo., USA) was added and mixed at 700 rpm to swell the cellulose. Vial was heated at 180° C. for 1 h. 50 µL of water was added for analysis by HPLC. Yield of HMF was 49.8%.

EXAMPLE 10

Conversion of Cellulose in [EMIM]Cl

CrCl$_3$ Metal Halide Catalyst

Cellulose was processed as in Example 9 in [EMIM]Cl at 140° C. for 0.5 h. Metal halide catalyst was CrCl$_3$. Products were analyzed by HPLC. Yield of HMF was 50.7%; yield of levulinic acid was 1.4%; yield of formic acid was 2.5%. Results for Examples 9-10 are listed in TABLE 4.

TABLE 4

Conversion of Cellulose to HMF, and product yields.

| Example | Feedstock | Process conditions for hydrolysis and dehydration | Feedstock conversion (%) | Product yields (%) |
|---|---|---|---|---|
| 9 | Cellulose | Temp: 180° C., Time: 3 h Catalyst: CrCl$_2$ | — | HMF: 49.8 |
| 10 | Cellulose | Temp: 140° C., Time: 0.5 h, Catalyst: CrCl$_3$ | — | HMF: 50.7 Levulinic acid: 1.4 Formic acid: 2.3 |

EXAMPLE 11

Conversion of Sorbitol in [OMIM]Cl

No Metal Halide Catalyst 50 mg sorbitol and 500 mg [OMIM]Cl were introduced to a vial. The vial was installed into a high pressure reactor, evacuated, purged with $N_2$. The vial was shaken at 700 rpm and heated at 150° C. under 25-torr vacuum for 1 h. The vial was cooled and 2.0 mL water was added for analysis by HPLC. Conversion of sorbitol was 97.2%, yield of 1,4-sorbitan was 51.6%; yield of isosorbide was 20.0%.

EXAMPLE 12

Conversion of Sorbitol in [OMIM]Cl

$CuCl_2$ Metal Halide Catalyst

Sorbitol was processed as in Example 9 in [OMIM]Cl with 50 mg $CuCl_2$ added as catalyst. Conversion of sorbitol was 95.8%; yield of 1,4-sorbitan was 36.3%; and yield of isosorbide was 37.3%.

EXAMPLE 13

Conversion of Sorbitol in [EMIM]$CH_3SO_3$

No Metal Halide Catalyst

Sorbitol was processed as in Example 9 in [EMIM]$CH_3SO_3$. Liquid products were analyzed by HPLC. Conversion of sorbitol was 82.4%; yield of 1,4-sorbitan was 63.8%; yield of isosorbide was 1.6%.

EXAMPLE 14

Conversion of Sorbitol in [EMIM]Cl

$ZnCl_2$ Metal Halide Catalyst

Sorbitol was processed as in Example 9 in [EMIM]Cl with 50 mg $ZnCl_2$ added as catalyst. Products were analyzed by HPLC. Conversion of sorbitol was 92.1%; yield of 1,4-sorbitan was 76.0%; yield of isosorbide was 3.8%.

Results of Examples 11-14 are summarized in TABLE 5.

TABLE 4

Conversion of Sorbitol, and product yields.

| Example | Feedstock | Ionic Liquid and Catalyst | Feedstock conversion (%) | Product yields (%) |
|---|---|---|---|---|
| 11 | Sorbitol | IL: [OMIM]Cl, Catalyst: None | 97.2 | 1,4-sorbitan: 51.6 Isosorbide: 20.0 |
| 12 | Sorbitol | IL: [OMIM]Cl, Catalyst: $CuCl_2$ | 95.8 | 1,4-sorbitan: 36.3 Isosorbide: 37.3 |
| 13 | Sorbitol | IL: [EMIM]$CH_3SO_3$, Catalyst: None | 82.4 | 1,4-sorbitan: 63.8 Isosorbide: 1.6 |
| 14 | Sorbitol | IL: [EMIM]Cl, Catalyst: $ZnCl_2$ | 92.1 | 1,4-sorbitan: 76.0 Isosorbide: 3.8 |

As demonstrated in Examples 11-14, sorbitol is dehydrated to products including, e.g., isosorbide and 1,4-sorbitan. Yields are selectively tunable by choices of ionic liquid and catalyst.

While Examples presented herein demonstrate conversion of carbohydrates using a single batch process and reactor, the invention is not limited thereto. Those of skill in the art will appreciate that many reactors and reactor configurations are suitable for use in conjunction with the invention, including, e.g., step-wise and/or serial processing, multistage processing and reactors, continuous flow processing and reactors, and/or tandem stage processing and reactors. All reactor configurations and processes as will be contemplated and implemented by those of skill in the art in view of the present disclosure are within the scope of the invention.

While preferred embodiments of the invention have been shown and described herein, many changes and modifications may be made without departing from the invention in its broader aspects. The appended claims are therefore intended to cover all such changes and modifications as fall within the scope of the invention.

We claim:

1. A method for selective conversion of a fructose to produce a furan, said method comprising the steps:

mixing fructose up to a limit of solubility with an ionic liquid, said ionic liquid a 1-$R_1$-3-$R_2$-imidazolium chloride, where $R_1$ and $R_2$ are alkyl groups of formula ($C_xH_{2x+1}$) where X=1 to 18; and heating said fructose in the presence of a metal halide catalyst at a reaction temperature and a reaction time sufficient for conversion of same.

2. The method of claim 1, wherein said metal halide is selected from the group consisting of $AlCl_3$, $CrCl_2$, $CrCl_3$, $FeCl_2$, $FeCl_3$, CuCl, CuBr, $CuCl_2$, $CuBr_2$, $VCl_3$, $MoCl_3$, $PdCl_2$, $PtCl_2$, $PtCl_4$, $RuCl_3$, $RhCl_3$, and combinations thereof.

3. The method of claim 1, wherein said reaction temperature is about 80° C. and said reaction time is between about 1 hour and about 4 hours.

4. The method of claim 1, wherein conversion of fructose is greater than or equal to about 80 percent and said yield of said furan is greater than or equal to about 50 percent on a mole basis.

5. The method of claim 1, wherein said yield of said furan is at least about 35 percent by weight.

6. The method of claim 1, wherein yield of levulinic acid and α-angelicalactone is less than about 3 percent by weight.

7. The method of claim 1, wherein the step of heating said carbohydrate includes a reaction time of from about 0.01 minutes to about 5 hours and a reaction temperature of from about 400° C. down to about 20° C.

8. The method of claim 1, wherein the step of heating said carbohydrate includes a reaction time and a reaction temperature of between about 0.01 minutes at about 250° C. and about 12 hours at about 20° C.

9. A method for selective conversion of a carbohydrate to produce a furan, said method comprising the steps:

mixing said carbohydrate up to a limit of solubility with an ionic liquid; wherein said ionic liquid includes a cation of chemical formula 1-$R_1$-3-$R_2$-imidazolium where $R_1$ and $R_2$ are alkyl groups of formula ($C_xH_{2x+1}$) where X=1 to 18, and an anion; said anion selected from the group consisting of methanesulfonate and trifluoromethanesulfonate; and heating said carbohydrate in the presence of a catalyst at a reaction temperature and a reaction time sufficient for conversion of same.

10. A method for selective conversion of a carbohydrate to produce a furan, said method comprising the steps:

mixing said fructose up to a limit of solubility with 1-ethyl-3-methylimidazolium methanesulfonate; and heating said fructose in the presence of methane sulfonate or its conjugate acid at about 80° C. for 2 hours and about 30° C. for 12 hour.

* * * * *